(12) United States Patent
Kullen et al.

(10) Patent No.: US 6,242,194 B1
(45) Date of Patent: Jun. 5, 2001

(54) ACID-INDUCIBLE PROMOTERS FOR GENE EXPRESSION

(75) Inventors: Martin J. Kullen; Todd R. Klaenhammer, both of Raleigh, NC (US)

(73) Assignee: North Carolina State University, Raleigh, NC (US)

(*) Notice: Subject to any disclaimer, the term of this patent is extended or adjusted under 35 U.S.C. 154(b) by 0 days.

(21) Appl. No.: 09/637,968

(22) Filed: Aug. 11, 2000

Related U.S. Application Data

(63) Continuation of application No. 09/336,861, filed on Jun. 21, 1999, now abandoned.

(51) Int. Cl.[7] .............................. C12Q 1/68; C12P 21/04; C12N 1/20; C12N 15/00; C07H 21/04
(52) U.S. Cl. ..................... 435/6; 435/252.3; 435/252.9; 435/320.1; 435/471; 536/23.1; 536/24.1
(58) Field of Search .................... 435/6, 7.32, 69.1, 435/91.1, 91.31, 91.4, 91.5, 252.3, 252.9, 320.1, 476, 489, 853; 514/44; 536/23.1, 23.5, 24.1, 24.5, 25.3

(56) References Cited

U.S. PATENT DOCUMENTS

| | | |
|---|---|---|
| 5,529,908 | 6/1996 | Palva et al. . |
| 5,593,885 | 1/1997 | Klaenhamer et al. . |
| 5,618,723 | 4/1997 | Kaenhammer et al. . |
| 5,773,692 | 6/1998 | Johnson-Flanagan et al. . |
| 5,837,509 | 11/1998 | Israelsen et al. . |
| 5,994,077 | 11/1999 | Valdivia et al. . |

OTHER PUBLICATIONS

M.J. Kullen et al.; Use of Differential Display RT–PCR to Identify Conditionally Expressed Genes in *Lactobacillus Acidophilus*, Abstract, American Society for Microbiology, *ASM Conference on Small Genomes*, pp. 29–30 and cover page, Sep. 20–24, 1998 at Lake Arrowhead, California.

O'Sullivan et al.; Relationship Between Acid Tolerance, Cytoplasmic pH, and ATP and $H^+$–ATPase Levels in Chemostat Cultures of *Lactococcus Lactis*, Applied and Environmental Microbiology, 65(6):2287–2293 (Jun. 1999).

Collins et al.; Selection of Probiotic Strains for Human Applications, *Int. Dairy Journal*, 8:487–490 (1998).

Mary Ellen Sanders; Overview of Functional Foods: Emphasis on Probiotic Bacteria, *Int. Dairy Journal*, 8:341–347 (1998).

Madsen et al.; Molecular Characterization of the pH–Inductible and Growth Phase–Dependent Promoter P170 of *Lactococcus Lactis*, Molecular Microbiology, 32(1):75–87 (1999).

Primary Examiner—John L. LeGuyader
Assistant Examiner—Jane Zara
(74) Attorney, Agent, or Firm—Myers Bigel Sibley & Sajovec

(57) ABSTRACT

An isolated polynucleotide encoding an acid-inducible, or acid-responsive, promoter element includes the $F_1F_0$-ATPase promoter of *Lactobacillus acidophilus* DNA that hybridizes thereto and encodes an acid-inducible promoter. Recombinant molecules comprising the promoter operatively associated with a DNA of interest, along with vectors and host cells containing the same, are also disclosed. Methods of upregulating the transcription of a DNA of interest in a host cell with such promoters are also disclosed.

22 Claims, 7 Drawing Sheets

```
              10         20         30         40         50
         ....|....|....|....|....|....|....|....|....|....|
700396   CGGTACTAAG TAAACACCTT TTCACAAAAA ATATTACTC TAATGCGCTT 60         70         80         90        100
         ....|....|....|....|....|....|....|....|....|....|
700396   TCATTTTACA CAAAGAAGAT ATTGGTGTT AAGATGATTT ACGTGTTCGA 110        120        130
         ....|....|....|....|....|....|
700396   GTTTATTCA ACACGAGAAG GGAGGTCACG AAGTA (SEQ. ID NO:1)
```

FIG. 1

5' CGGTACTAAGTAAACACCTTTCACAAAAATATTTACTCTAATGGCTTTCA

-35                    Ext. -10      +1
TTTACACAAAGAAGATATATTGGTGTTAAGATGATTACGTGTTCGAGTTTTAT

TCAACACGAGAAGGGAGGTCACGAAGTA 3' (SEQ. ID NO:1)

ACID-INDUCIBLE PROMOTERS FOR GENE EXPRESSION

This application is a continuation of application Ser. No. 09/336,861, filed Jun. 21, 1999, now abandoned the disclosure of which is incorporated by reference herein in its entirety.

FIELD OF THE INVENTION

The present invention concerns promoter elements in general, along with DNA constructs comprising such promoters operably associated with a DNA in a recombinant DNA molecule, host cells containing the same, and methods of using the same.

BACKGROUND OF THE INVENTION

The gastrointestinal tract is the most densely colonized region of the human body (Savage, *Ann. Rev. Microbiol.* 31, 107 (1977); Tannock, Normal microflora (Chapman and Hall, London 1995)) and the accumulated evidence indicates that this collection of microbes has a powerful influence on the host in which it resides. Comparisons between germ free and conventional animals have shown that many biochemical, physiological and immunological functions are influenced by the presence of the diverse and metabolically active bacterial community residing in the gastrointestinal tract (Marteau and Rambaud, *FEMS Microbiol. Rev.* 12, 207 (1993); Norin et al., *Appl. Environ. Microbiol.* 74, 1850 (1991); Tannock, supra). Lactobacilli are important residents of the microflora (Ahrne et al., *J. Appl. Microbiol.* 85, 88 (1998); Kimura et al., *Appl. Environ. Microbial.* 63, 3394 (1997)), and have been the subject of intense and growing interest because of their possible role in the maintenance of gastrointestinal health (Bengmark, *Gut* 42, 2 (1998)). Of immense importance to lactobacilli functioning in this role is the ability to endure in the harsh conditions of the gastrointestinal tract, where the gastric pH frequently falls below 2.0 in healthy individuals (McLauchlan et al., *Gut* 30, 573 (1998)).

Changes in extracellular pH have been shown to influence the expression of a variety of genes from many different bacteria (reviewed in Olson, *Mol. Microbiol.* 8, 5 (1993)). In the presence of a low external pH (<3.5), *L. acidophilus* is able to maintain cytoplasmic pH at values close to neutral (Kashket, *FEMS Microbiol. Rev.* 46, 233 (1987)). However, the mechanisms by which *L. acidophilus* responds and adapts to extremely acidic conditions remain poorly defined, For several organisms that inhabit the gastrointestinal tract, the $F_1F_0$-ATPase is an important element in the response and tolerance to low pH. In the fermentative bacterium, *Enterococcus* (En.) *hirae*, maintenance of cytoplasmic pH has been shown to occur via amplification of the proton translocating ATPase (Kobayashi et al., *J. Bacteriol.* 158, 1157 (1984); Kobayashi et al., *J. Biol. Chem.* 261, 627 (1986)). Similarly, a short exposure of *Salmonella typhimurium* to pH 6.0 induces the synthesis of the $F_1F_0$-ATPase (Foster and Hall, *J. Bacteriol.* 173, 5129 (1990); Foster and Hall, *J. Bacteriol.* 172, 771 (1990)). Nanen and Hutkins (*J. Dairy Sci.* 74, 747 (1991)) have demonstrated that the specific activity of $H^+$-ATPases from several lactic acid bacteria increases as the extracellular pH moves from neutral to 5.0. Alternatively, changes in environmental pH appear to have little influence on the expression of the atp operon, whose genes code for the various subunits of the $H^+$-ATPase, in *Escherichia coli* (Kasimoglu et al., *J. Bacteriol.* 178, 5563 (1996)). Likewise, expression of the atp operon of *Bacillus subtilis* appears to be constitutive (Santana et al., *J. Bacteriol.* 176, 6802 (1994)).

The identification of conditionally expressed genes provides a wealth of insight into the physiological consequences of and responses to a given stimulus. In the case of *L. acidophilus*, a significant challenge remains in understanding the intestinal roles and activities of this organism. An important element in this regard is the determination of which characteristics are important for the survival and success of this organism in the gastrointestinal tract. While differential display (Liang and Pardee, *Science* 257, 967 (1992); Welsh et al., *Nucleic Acids Res.* 20, 4965 (1992)) has been used extensively to identify conditionally expressed genes in eukaryotes, the application of this methodology in prokaryotes has not been explored to a comparatively significant extent (Abu Kwaik and Pederson, *Mol. Microbiol.* 21, 543 (1996); Fislage, *Electrophoresis* 19, 613 (1998); Fislage et al., *Nucleic Acids Res.* 25, 1830 (1997); Wong and McClelland, *Proc. Natl. Acad. Sci. USA* 91, 639 (1994); Zhang and Normark, *Science* 273, 1234 (1996)). Practical problems with the method are presented by: the relatively large proportion of structural RNA species in the total RNA; the low level of polyadenylation of mRNA (Sarkar, *Ann. Rev. Biochem.* 66, 173 (1997)), which prohibits the use of 3' dT anchored primers; and the structural instability and short half life of low abundance mRNA species of prokaryotes as compared to eukaryotes (Higgins et al., *Curr. Opin. Genet. Dev.* 2, 739 (1992)).

SUMMARY OF THE INVENTION

A first aspect of the present invention is an isolated polynucleotide encoding an acid-inducible, or acid-responsive, promoter element. The promoter element may be:

(a) DNA having the sequence:
CGGTACTAAG TAAACACCTT TTCACAAAAA ATATTT ACTC TAATGCGCTT TCATTTTACA CAAAGA AGAT ATTTGGTGTT AAGATGATTT ACGTGTTCGA GTTTTATTCA ACACGAGAAG GGAGGTCACG AAGTA (SEQ ID NO: 1), comprising the $F_1F_0$-ATPase promoter of *Lactobacillus acidophilus*; or (b) DNA that hybridizes to DNA of (a) above (e.g., under stringent conditions) and encodes an acid-inducible promoter.

Preferably, the promoter is a proton ($H^+$) translocating ATPase promoter, and preferably the promoter is an F-type ATPase promoter.

The acid responsive promoter of the invention has applications in a number of scenarios. The promoter may be used for the expression of gene products during the normal course of fermentation by cells such as bacterial cells, particularly lactic acid bacteria, in dairy, meat, vegetable, cereal, and other bioconversions. The promoter may be used for the induction of gene products upon exposure of lactic acid bacteria to acid environments, including suspension into acidified foods or entry into the gastrointestinal tract or other body cavities as a probiotic bacteria.

The promoter may be used for the acid-responsive expression of enzymes, vaccines, proteins, peptides, etc. from lactic acid bacteria intended to serve as delivery or production systems. Specific examples include: Acid-induced expression of lactase expression from Lactobacillus species in the stomach or gastrointestinal tract (GIT) to facilitate lactose digestion; Acid-induced expression of vaccines from Lactobacillus or Lactococcal species in the appropriate body cavity in order to promote immunological responses and oral-induced mucosal immunity; acid-induced expression of holins/lysins to promote bacteria cell lysis or permeability and, thereby, release any of the above compounds into food, bioreactors, or the GIT of man or animals.

Accordingly, a second aspect of the invention is a recombinant DNA molecule comprising a promoter operably associated with a DNA of interest, wherein said promoter is an acid inducible promoter as described above. The DNA of interest may encode a protein or peptide, the production of which is upregulated upon induction, may encode an antisense oligonucleotide that causes the downregulation of a different gene upon induction of the acid inducible promoter, may encode a ribozyme, etc.

A third aspect of the invention is a vector (e.g., a plasmid) comprising a recombinant DNA molecule as described above.

Further aspects of the invention include a method of transforming a cell comprising providing a vector as described above and then transforming said cell with said vector, along with recombinant DNA molecules as described above. Where the DNA of interest is to be transcribed within the cell, the cell may be one in which the promoter is operable (that is, induced by acid pH as described herein, or simply constitutively active). The DNA of interest may be from a different organism than the host cell (that is, a heterologous DNA of interest), or may be from the same organism as is the host cell, although in a recombinant DNA molecule (in which case the recombinant DNA is heterologous in that it is not naturally occurring in the host cell).

A still further aspect of the invention is a method of controlling the transcription of a DNA of interest, comprising: (a) providing a cell culture at neutral or basic pH conditions, said culture comprising a cell containing a recombinant DNA molecule, said recombinant DNA molecule comprising a promoter operably associated with a heterologous DNA of interest, wherein said promoter is an acid inducible promoter as described above; and then (b) reducing said pH to acidic conditions so that transcription of said heterologous DNA of interest induced by said promoter is increased as compared to the level of transcription of said heterologous DNA of interest induced by said promoter when said pH is at neutral or more basic conditions. The DNA of interest may encode an desired molecule, such as a protein or peptide (which is both transcribed and translated in the cell), an antisense oligonucleotide, a ribozyme, etc. The reducing step may be carried out by any suitable means, including but not limited to adding an exogenous acid to the culture, administering the culture to an acidic body cavity of a subject, producing by fermentation an acid in the culture, etc.

The foregoing and other objects and aspects of the invention are described in the drawings herein and the specification set forth below.

BRIEF DESCRIPTION OF THE DRAWINGS

FIG. 1. DNA sequence of the pH-inducible promoter, $P_{311AD}$, from L. acidophilus NCFM/N2 from L. acidophilus ATCC 700396. Promoter region was PCR-amplified, cloned and sequenced.

DETAILED DESCRIPTION OF PREFERRED EMBODIMENTS

Figure 2:
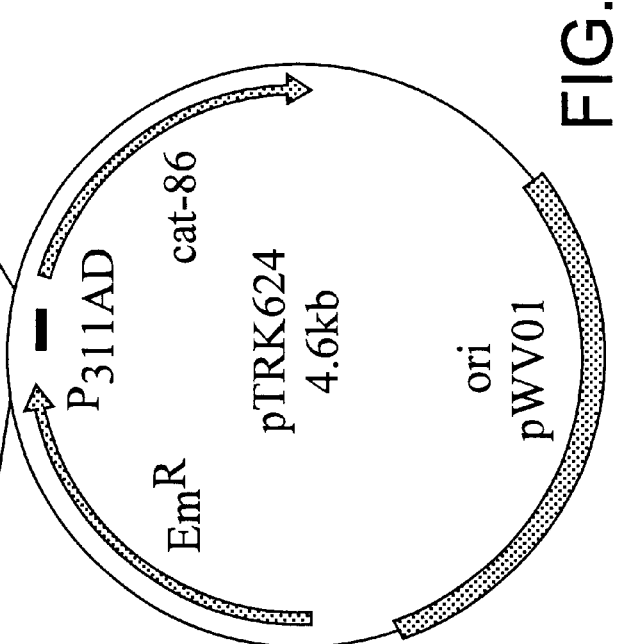
FIG. 2. Schematic representation of pTRK624 (previously p311AD) promoter construct and DNA sequence of $P_{311AD}$. Salient features (−35, −10 and +1) of the promoter are underlined and denoted. The sequence shown is SEQ ID NO: 1.

Nucleotide sequences are presented herein by single strand only, in the 5' to 3' direction, from left to right. Nucleotides are represented herein in the manner recommended by the IUPAC-IUB Biochemical Nomenclature Commission, in accordance with 37 CFR §1.822 and established usage. See, e.g., PatentIn User Manual, 99–102 (November 1990) (U.S. Patent and Trademark Office).

"Acid-inducible" (pH inducible, acid-responsive) as used herein with respect to a promoter refers to a promoter that is (a) substantially silent or silent and does not drive substantial levels of transcription when contained in a cell at an extracellular pH of 7 (in that a DNA operatively associated with said promoter is not transcribed or transcribed at low "leakage" levels), and (b) is active and drives transcription of a DNA operatively associated therewith when contained in a cell, which cell is in contact with an extracellular environment having a pH less than 7 (e.g., 6, 5, 4, 3), at substantially greater levels than that driven at an extracellular pH of 7 or more. In addition, "acid-inducible" as used herein refers to a promoter that is (a) active and does drive transcription when contained in a cell at an extracellular pH of 7, and (b) is more active and drives transcription of an associated DNA when contained in a cell which cell is at an extracellular pH less than 7 as described above, at substantially greater levels as compared than that driven at an extracellular pH of 7 or more. It is not required that the promoter be acid inducible in all host backgrounds. For example, the promoter of SEQ ID NO:1 herein is not acid inducible in Escherichia coli, but still functions as a constitutively active promoter and is useful as such in E. coli.

"Operably linked" and "operably associated", when used with reference to nucleotide regions, refer to regions that are functionally related to each other usually on the same nucleotide molecule. For example, a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading frame.

1. Promoters

The invention describes the use of an acid-inducible promoter element to allow for expression of heterologous genes by lactic acid bacteria at low pH. The expression system is comprised Of $P_{311AD}$, the promoter of the acid-inducible atp operon of Lactobacillus acidophilus, and the gene(s) to be expressed. The promoter element is 135 bp, found in Lactobacillus acidophilus and ATCC 70396 (FIGS. 1–2; SEQ ID NO: 1), and located upstream of the F1F0-ATPase operon. Homologous DNA sequences were located in Lactobacillus gasseri and Lactobacillus johnsonii, but not in Lactococcus lactis. The promoter is functional and inducible at low pH by either lactic acid and hydrochloric acid and can drive expression of heterologous genes in both Lactococcus and Lactobacillus species as acid develops during a fermentation, or upon exposure of the above cultures to acid.

Other acids that can be used to induce the promoter, in addition to those naturally present in vitro in a fermentation or in vivo in the gut of an animal, include, but are not limited to, phosphoric acid, maleic acid, malic, propionic, citric, HCl, $H_2SO_4$, lactic, acetic, butyric, succinic, etc. The step of reducing the pH may be carried out by adding the acid by any suitable means, including the addition of exogenous acids, and by causing the production of acids from cells in the culture to produce sufficient acid to lower the pH, or by acids found in the gastrointestinal tract of the animal. Where used in food fermentations or fermentations for the production of pharmacuetical compounds, exogeneously added acids are preferably those meeting "Generally Regarded as Safe" (GRAS) criteria.

Promoters or polynucleotides of the present invention include those coding for promoters homologous to, and having essentially the same biological properties as, the promoters disclosed herein as SEQ ID NO:1 and encoding an acid inducible promoter. This definition is intended to encompass natural allelic sequences thereof. Thus, isolated DNA or cloned genes of the present invention can be of any species of origin, but are preferably of bacterial origin. Thus, polynucleotides that hybridize to DNA disclosed herein as SEQ ID NO:1 (or fragments or derivatives thereof which serve as hybridization probes as discussed below) and which code on expression for a acid inducible promoter, (particularly an F-type ATPase promoter), are also an aspect of the invention. This includes extension products and fragments of SEQ ID NO:1 that retain activity as an acid-inducible promoter. Conditions which will permit other polynucleotides that code on expression for a protein of the present invention to hybridize to the DNA of SEQ ID NO:1 disclosed herein can be determined in accordance with known techniques. For example, hybridization of such sequences may be carried out under conditions of reduced stringency, medium stringency or even stringent conditions (e.g., conditions represented by a wash stringency of 35–40% Formamide with 5×Denhardt's solution, 0.5% SDS and 1×SSPE at 37° C.; conditions represented by a wash stringency of 40–45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C.) to DNA of SEQ ID NO:1 in a standard hybridization assay. See, e.g., J. Sambrook et al., Molecular Cloning, *A Laboratory Manual* (2d Ed. 1989) (Cold Spring Harbor Laboratory).

Lactobacillus acidophilus ATCC 70396, having ATCC accession number 70396, was previously deposited with the American Type Culture Collection and was converted to a deposit in accordance with the Budapest Treaty on Jun. 4, 1999 at the American Type Culture Collection (ATCC) at 10801 University Boulevard, Manassas (Va.), 20110-2209 USA.

Isolated L. acidophilus bacteria having all of the identifying characteristics of the foregoing of ATCC 70396 bacterial strain, cultures thereof, and DNA derived therefrom are also an aspect of this invention.

2. DNA Constructs

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicant specifically intends that the disclosure of all patent references cited herein be incorporated herein in their entirety by reference).

A vector is a replicable DNA construct. Vectors are used herein either to amplify DNA encoding the proteins of the present invention or to express the proteins of the present invention. An expression vector is a replicable DNA construct in which a DNA sequence encoding the proteins of the present invention is operably linked to suitable control sequences capable of effecting the expression of proteins of the present invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegaloviris), phage, retroviruses and integratable DNA fragments (i.e., fragments integratable into the host genome by recombination). The vector replicates and functions independently of the host genome, or may, in some instances, integrate into the genome itself. The vector may be a microparticle that carries the DNA construct for ballistic bombardment of cells. Expression vectors should contain a promoter and RNA binding sites that are operably linked to the gene to be expressed and are operable in the host organism.

The particular manner in which host cells are transformed will depend upon the particular host cell and vector system. In general, transformation can be carried out by infection, electroporation, ballistic bombardment, natural competence, artificial competence, protoplast transformation, etc.

3. Fermentative Microorganism Host Cells

While the present invention is, in a preferred embodiment, directed to the fermentation of food, the invention may be practiced with any fermentation process, preferably so long as the promoter is inducible in the host cell. See generally Prescott and Dunn's Industrial Microbiology (G. Reed Editor 4th Ed. 1982); Food Biotechnology (Y. Hui and G. Khachatourians Eds. 1995). Thus, the host cell may be an animal (e.g., avian, mammalian), plant (e.g., monocot, dicot), yeast, or bacterial (e.g., gram negative or gram positive) host cell. Lactic acid producing bacteria are preferred.

Exemplary fermentation systems and the corresponding host cells in which they may be used include, but are not limited to, those for cheddar and cottage cheese (*Lactococcus lactis, Lactococcus cremoris*), Yogurt (*Lactobacillus bulgaricus, Streptococcus thermophilus*), Swiss cheese (*S. thermophilus, Lactobacillus lactis, Lactobacillus helveticus*), Blue cheese (*Leuconostoc cremoris*), Italian cheese (*L. bulgaricus, S. thermophilus*), Viili (*Lactococcus cremoris, Lactococcus lactis* subsp. *diacetylactis, Leuconostoc cremoris*), Yakult (*lactobacillus casei*), casein (*Lactococcus cremoris*), Natto (*Bacillus subtilis* var. *natto*), Wine (*Oenococcus oenos*), Sake (*Leuconostoc mesenteroides*), Polymyxin (*Bacillus polymyxa*), Colistin (*Bacillus colistrium*), Bacitracin (*Bacillus licheniformis*), L-Glutamic acid (*Brevibacterium lactofermentum, Microbacterium ammoniaphilum*), and acetone and butanol (*Clostridium acetobutylicum, Clostridium saccharoperbutylacetonicum*). See generally M. Sanders, Bacteriophages of Industrial Importance, in PHAGE ECOLOGY, 211–44 (S. Goyal, C. Berba and G. Bitton eds. 1987). Thus, the present invention may, for example, be employed in a fermentation process for producing any of the foregoing products (food products and other) with the foregoing bacteria in the manner described herein.

Bacteria capable of fermenting foods include those bacteria used in any type of food fermentation, including, but not limited to, the fermentation of milk, egg, meat, fruit, vegetables, and cereals. See generally Food Biotechnology, (D. Knorr Ed. 1987)(Marcel Dekker, Inc.); Fermented Foods (A. Rose Ed. 1982)(Academic Press); C. Pederson, Microbiology of Fermented Foods, (2d ed. 1 979)(AVI Publishing Co.).

Milk is fermented to produce products such as cheese, yoghurt, kefir, and acidophilus milk. Cheese fermentation bacteria are discussed separately below. Otherwise, bacteria used for the fermentation of milk include, but are not limited to, *Lactobacillus bulgaricus, Lactobacillus acidophilus, Streptococcus thermophilus,* and mixtures thereof. See Food Biotechnology, 530 (D. Knorr Ed. 1987); C. Pederson, Microbiology of Fermented Foods, 105–35 (2d ed. 1979).

Bacteria used for the fermentation of milk to produce cheese include, but are not limited to, *Lactobacillus bulgaricus, Lactobacillus helveticus, Streptococcus thermophilus, Lactococcus lactis* subsp. *lactis, Lactococcus lactis* subsp. *cremoris, Lactococcus lactis* subsp. *lactis* biovar. *diacetylactis,* and mixtures thereof. See Food Biotechnology, 530 (D. Knorr Ed. 1987); C. Pederson, Microbiology of Fermented Foods, 135–51 (2d ed. 1979).

Bacteria used for the fermentation of egg include *Pediococcus cerevisiae, Lactobacillus plantarum,* and mixtures thereof. See Food Biotechnology, 538–39 (D. Knorr Ed. 1987).

Bacteria used for the fermentation of meat (including beef, pork, and poultry) include, but are not limited to, Lactic acid bacteria, *Pediococcus cerevisiae, Lactobacillus plantarum, Lactobacillus brevis,* Micrococcus species, *Leuconostoc citrovorum,* and mixtures thereof. See Food Biotechnology, 538–39 (D. Knorr Ed. 1987); C. Pederson, Microbiology of Fermented Foods, 210–34 (2d ed. 1979); U.S. Pat. No. 2,225,783 to Jensen and Paddock.

Bacteria used for the fermentation of vegetables (e.g., carrots, cucumbers, tomatoes, peppers, and cabbage) include, but are not limited to, *Lactobacillus plantatum, Lactobacillus brevis, Leuconostoc mesenteroides, Pediococcus cerevisiae,* and mixtures thereof See Food Biotechnology, 540 (D. Knorr Ed. 1987); C. Pederson, Microbiology of Fermented Foods, 153–209 (2d ed. 1979); U.S. Pat. No. 3,024,116 to Engelland; U.S. Pat. No. 3,403,032 to Etchells et al.; U.S. Pat. No. 3,932,674 to Etchells et al.; U.S. Pat. No. 3,897,307 to Porubcan et al.

Bacteria used in the fermentation of dough formed from cereals (e.g., wheat, rye, rice, oats, barley, and corn) include yeasts such as *Saccharomyces cerevisiae* and *Candida utilis;* and lactic acid bacteria of the genera Lactobacillus, Lactococcus, Pediococcus and Leuconostoc, including, but not limited to *Lactobacillus delbrueckii, Lactobacillus leichmanni, Lactobacillus plantarum, Lactobacillus casei, Lactobacillus brevis, Lactobacillus fermenti, Lactobacillus pastorianus, Lactobacillus buchneri,* and *Leuconostoc mesenteroides.* See generally Food Biotechnology, 235–70 (D. Knorr Ed. 1987); U.S. Pat. No. 3,734,743 to Kline and Sugihara; U.S. Pat. No. 3,681,083 to Everson; U.S. Pat. No. 3,993,783 to Khoudokormoff and Langejan; U.S. Pat. No. 3,843,800 to Langejan; U.S. Pat. No. 3,410,692 to Wutzel.

Wine is produced by the fermentation of fruit juice, typically grape juice, with yeasts, such as *Saccharomyces cerevisiae* and *Saccharomyces ellipsoideus,* as well as with a broad variety of lactic acid bacteria including *Pediococcus cerevisiae, Lactobacillus plantarum, Leuconostoc mesenteroides, Leuconostoc dextranicum, Leuconostoc cremoris, Lactobacillus brevis,* and *Lactobacillus fermenti.* Beer is produced by the fermentation of malt with yeasts such as *Saccharomyces cerevisiae* and *Saccharomyces carlsbergensis.* See C. Pederson, Microbiology of Fermented Foods, 271–309 (2d ed. 1979).

In a particularly preferred embodiment, the present invention is employed for the fermentation of milk with Lactococci (previously classified as the group N Streptococci), such as *Lactococcus lactis* subsp. *lactis, Lactococcus lactis* subsp. *cremoris,* and *Lactococcus lactis* subsp. *lactis* biovar. *diacetylactis.*

Other host cells that are used in industrial fermentation to produce proteins or peptides of interest, including pharmaceutical proteins and peptides, include, but are not limited to, mammalian (e.g., human, mouse, rat, monkey), avian (e.g., chicken, turkey), plant (including monocot and dicot), plant systems such as duckweed, yeast, and other gram negative and gram positive bacteria such as *Escherichia coli,* and *Bacillus subtilis.*

As noted above, the DNA of interest may encode a protein or peptide, or may encode another molecule such as an antisense oligonucleotide or a ribozyme, the production of which is desired to be upregulated during the fermentation process. Hence, the term "fermentation" is to be construed as any process involving the growth or maintenance of bacterial cells, and not simply to the active production of a particular protein or peptide product by bacterial action.

In a microbiological fermentation process, the acid can be added exogeneously, or can be added by the fermentative or microbiological production of the acid by the microbiological culture itself. Thus, in one embodiment, the DNA of interest is not expressed until such time in the fermentation process as sufficient acid has been produced. Note that the acid may be produced by the same cells that are host to the DNA of interest or (in a mixed culture) may be produced by different cells than that carrying the DNA of interest.

Starter cultures employed in practicing the present invention may be in any physical form, including liquid cultures of the fermentation bacteria in a suitable growth medium, as well as lyophilized cultures and frozen cultures prepared therefrom. The cultures may be provided in a suitable container, such as a flexible foil or polymer package, a bottle, vial or jar, etc. Starter cultures employed in the present invention are preferably defined cultures (i.e., cultures of known bacterial content). Such defined cultures may be either single strain cultures or multiple strain cultures.

4. Probiotic Bacterial Host Cells

As noted above, in one embodiment of the invention the host cell is selected to colonize a body cavity such as the gastrointestinal tract (GIT or "gut", including but not limited to stomach, small intestine, and large intestine) of an animal subject to which the host cell is administered. In such cases the host cell is referred to as a probiotic bacteria. See generally J. Collins et al., Selection of Probiotic Strains for Human Applications, *Int. Dairy Journal* 8, 487(1998); M. Sanders, Overview of Functional Foods: Emphasis on Probiotic Bacteria *Int. Dairy Journal* 8, 341 (1998); Probiotics: The Scientific Basis (Chapman & Hall, R. Fuller Ed. 1992; Probiotics 2: Applications and Practical Aspects (Chapman & Hall, R. Fuller ed. 1997). Preferably the body cavity is one that is characterized by an acid pH environment. In this embodiment the DNA of interest be expressed in the body cavity (e.g., the GIT) tract of a host subject (e.g., a human subject, or animal subjects such as chickens, turkeys, reptiles, cattle/cows, horses, etc.). Examples of probiotic bacteria that can be used to carry out the present invention, compositions of probiotics that can be used to carry out the present invention, and particular manners the use thereof, include, but are not limited to, those described in U.S. Pat. Nos. 5,879,719; 5,728,380; 5,705,152; 5,604,127; and 5,589,166 (the disclosures of all U.S. Patents cited herein are to be incorporated by refrence herein in their entirety). The probiotic bacteria can be administered to the animal subject by any suitable route, including but not limited to oral, nasal, vaginal, and anal routes of delivery.

Particular examples of probiotic bacteria include, but are not limited to, Lactobacillus species (e.g., *Lactobacillus acidophilus, L. gasseri, L. johnsonii, L. plantarum, L. reuteri, L delbrueckii, L. gallinarum, L. crispatus, L. casei, L. paracasei, L. rhamnosus,* and *L. sake*), Lactobacillus species (e.g., *Lactobacillus bulgaricus, Lactobacillus lactis*) *Streptococcus thermophilus,* Lactococcus species (e.g., *Lactococcus lactis* subsp. *lactis, Lactococcus lactis* subsp. *cremoris*); Bifidobacterium (including *B. bifidum, B. longum, B. infantis, B. breve, B. adolescentis, B. lactis,* and *B. angulatum*) *Enterococcus faecium, Pediococcus acidilactici, Pediococcus pentosaceus, Saccharomyces boulardii, Bacillus coagulans,* and *Leuconostoc mesenteroides*. Examples are given in Collins, et al, *Int. Dairy Journal* 8:487–490 (1998). The term "probiotic bacteria" is intended to include competitive exclusion media such as Salmonella competitive exclusion media, such as described in U.S. Pat. No. 5,340,577.

Probiotic bacteria host cells that contain a DNA of interest operably associated with a promoter of the invention can be orally administered to a subject to colonize the appropriate location in the gastrointestinal tract. Dosage and administration regime may be the same as with the untransformed probiotic bacteria and can be determined by routine procedures, depending upon the particular subject to which the probiotic is administered. Because of the acidic environment within the gastrointestinal tract, the DNA of interest will then be expressed therein. The DNA of interest may encode any suitable protein or peptide, including physiologically active proteins or peptides such as hormones, antibiotics (as long as they do not unduly interfere with the host cell from which they are expressed), Probiotic bacteria host cells can be combined with a pharmaceutically acceptable carrier such as water or saline solution for delivery to the subject. Where the intended route of delivery is an oral delivery, the carrier is preferably an edible carrier such as lactose, dried milk, mixtures thereof and the like. The probiotic bacteria can be combined with the carrier in any suitable amount depending upon the bacteria, purpose of administration, route of administration, subject, etc. For example, the probiotic bacteria may be included in the composition in an amount by weight of from 0.001 percent to 50 percent.

In the following examples, the use of differential display to identify genes expressed in *L. acidophilus* in response to low pH is described. From this analysis, the acid-responsive locus, atp, whose gene products code for the various subunits of the $F_1F_0$-ATPase, has been isolated. The pH-inducibility of the operon was verified by RNA hybridizations and was accompanied by an increase in the activity of the enzyme.

EXAMPLE 1

Use of Differential Display to Identify the pH-Inducible, Proton-translocating $F_1F_0$-ATPase (atpBEFHAGDC) Operon of *Lactobacillus acidophilus*

1. Experimental Procedures

Bacterial strains and plasmids. *L. acidophills* was grown in MRS (Difco) at 37° C. *E. coli* strains DH5α and XL1Blue were grown in Luria-Bertani (LB) broth at 37° C. with shaking or on LB broth supplemented with 1.5% agar. For selection of transformants, 5-bromo-4-chloro-3-indoyl-β-D-galactopyranoside, isopropyl-β-D-thiogalactopyranoside and ampicillin were included at concentrations of at 50, 200, and 100 μg/ml, respectively. PCR products were cloned initially into pGEM-T or pGEM-T Easy. Subcloning of PCR products was carried out in pGEM-7zf(+) (Promega).

DNA manipulations. *L. acidophilus* DNA was isolated as described previously (Walker and Klaenhammer, *J. Bacteriol.* 176, 5330 (1994)). Standard protocols were used for routine isolation of plasmid DNA from *E. coli,* ligations, endonuclease restrictions, DNA modification and transformation (Sambrook et al., Molecular cloning: A laboratory manual (2d ed. 1989)). Plasmid DNA used for sequencing was isolated using the QIAprep spin kit per the manufacturer's instructions (QIAGEN Inc.). PCR was preformed via standard protocols (Innis et al., PCR protocols: A guide to methods and applications (Academic Press 1990)). For the generation of PCR products to be sequenced, a proofreading polymerase (Expand High Fidelity; Expand Long Template; Boehringer Mannheim) was used. DNA sequencing on both strands of the template was performed with an ABI model 377 automated gene sequencer (Perkin-Elmer) or manually, with the ThermoSequenase™ kit (Amersham).

RNA manipulations. *L. acidophilus* was grown to an $OD_{600}$ of 0.6, at which time the pH of culture was adjusted to 3.5 with concentrated HCl. RNA was isolated from *L. acidophilus* at 0, 5, 15, 30, 45 and 60 minutes after exposure to pH 3.5 by using the TRIzol reagent (Gibco BRL) as has been described by Dinsmore and Klaenhammer (*J. Bacteriol.* 179, 2949 (1997)) and quantitated by spectrophotometric measurement at $OD_{260}$. For RNA slot blot hybridizations, total RNA (5 μg) from the different time points was denatured and blotted to a Zeta-Probe membrane (BioRad). The 0.7 kb differential display product was $^{32}P$ labeled by random priming and used as probe against the blotted RNA.

Hybridizations were carried out at 60° C. for 18 h. Autoradiographs were analyzed by densitometry using the Spot-Denso function with auto-linked background on an AlphaImager 2000 apparatus (Innotech Scientific Corp.).

Primer extension analysis. Five hundred ng of primer pxt1 (5' TAGCCGTTGAACCAATGATCCCAGTAAG 3')(SEQ ID NO: 2) was end labeled with 10 units of T4 polynucleotide kinase (Boehringer Mannheim) and 30 μCi [γ-$^{32}$P]ATP in a 50 μl reaction mixture. This mixture was incubated at 37° C. for 1 h and precipitated in the presence of 50 μg of different RNA samples isolated from L. acidophilus after exposure to pH 3.5 for 0, 30 and 45 min. The precipitated pellets were resuspended in hybridization solution (1M NaCl, 170 mM HEPES (pH 7.5), 330 mM EDTA (pH 8.0)). After incubation at 30° C. for 4 h, the hybridization solutions were precipitated and resuspended in a solution containing 200 U Superscript II Reverse Transcriptase (Gibco BRL), 40 U RNase Inhibitor (Boehringer Mannheim), 0.5 mM DTT, 1×first strand buffer and 10 mM each of dATP, dCTP, dGTP and dTTP. Extension reactions were carried out at 42° C. for 90 minutes, after which the labeled cDNAs were phenol extracted, precipitated and resuspended. Extension products were heat-denatured and analyzed on a denaturing polyacrylamide gel. A sequencing ladder of the same primer and a PCR product, containing the putative transcriptional start site (TSS), as template were run in adjacent lanes.

Differential Display. Ten μl samples containing 5 μg RNA from the different time points were DNaseI-treated (Gibco BRL) at 25° C. for 15 minutes. DNase was then inactivated by the addition of 1 μl of 25 mM EDTA and incubation at 65° C. for 10 minutes. Annealing of 100 pmol of the arbitrary primer, LADD3 (5' GTCATGTCAGA 3') (SEQ ID NO: 3), to DNase-treated RNA was done by heating the mixture to 70° C. and quickly chilling on ice. First-strand cDNA synthesis was carried out for 100 min at 42° C. in a 20 μl reaction containing 200 U Superscript II Reverse Transcriptase (Gibco BRL), 40 U RNase Inhibitor (Boehringer Mannheim), 0.5 mM DTT, 1×first strand buffer and 10 mM each of dATP, dCTP, dGTP and dTTP. The synthesized cDNA (3 μl) was amplified by PCR using the same primer and Taq DNA polymerase (Boehringer Mannheim) in the presence of 2.5 mM MgCl$_2$ in a Gene-Amp® PCR System 2400 thermal cycler (Perkin-Elmer) programmed for 5 min at 94° C. (initial denaturation) and 40 cycles of 30 sec at 94° C. (denaturation), 30 sec at 44° C., and 1 min at 72° C. (extension). PCR products were mixed with 8 μl of 80% formamide containing bromophenol blue and xylene cyanol, and heated to 70° C. for 10 min. Five μl of the denatured reaction mix were resolved by electrophoresis in 6.0% polyacrylamide-urea gel and visualized by silver staining according to the manufacturer's directions (Promega). Differential display products of interest were carefully excised from the rehydrated gel, soaked in 10 μl TE overnight and re-amplified by PCR using the conditions described above.

Cloning of the atp operon. A degenerate primer, based on a highly conserved region of amino acids ($^{273}$SAVGYQPT$^{280}$)(SEQ ID NO:4) in the β subunit (atpD) of E. coli (Saraste et al., Nucleic Acids Res. 9, 5287 (1981)), B. subtilis (Santana et al., J. Bacteriol. 176, 6802 (1994)) and Streptococcus spp. (Quivey et al., Gene 97, 63 (1991)), was used in conjunction with a primer derived from the sequence of the differential display product to direct PCR amplification of atpFHAGD. Regions that were positioned downstream of the amplicon containing atpFHAGD and those immediately upstream of the differential display product were cloned using the semi-random PCR chromosome walking approach described by Ge and Charon (Gene 189, 195 (1997)). The distal 5' region of the operon proved to be unclonable and was instead isolated using the single-specific primer PCR method, described by Shyamala and Ames (Gene 84, 1 (1989)), on an XbaI genomic library in pBluescript-II KS+. To facilitate sequencing and analysis, subclones of the operon were generated by PCR and restriction endonuclease digestion.

Preparation of membrane extracts and measurement of H$^+$-ATPase activity. Membrane extracts were prepared as described by Kobayashi et al. (J. Bacteriol. 158, 1157 (1984)) with modifications by Nannen and Hutkins (J. Dairy Sci. 74, 747 (1991)). H$^+$-ATPase activity was determined in duplicate by the colorimetric assay of inorganic phosphate liberated from ATP hydrolysis as described by Kobayashi and Anraku (J. Biochem. 71, 387 (1972)). One unit of ATPase was defined as μmol of P$_i$ generated per minute per mg protein at pH 5.25. Total protein was determined as described by Bradford (Anal. Biochem. 72, 248 (1976)).

2. Results

At different time intervals after the medium pH was adjusted to 3.5 with HCl, L. acidophilus RNA was isolated and expression was analyzed using differential display. Several products were present in the lanes containing treated cDNAs that were absent or considerably less abundant in the lane containing amplicons from untreated cells. The differentially displayed bands were carefully excised from the polyacrylamide matrix, re-amplified by PCR, cloned and sequenced. Using the sequence of the products to assess identity by BLAST searches (Altschul et al., Nucleic Acids Res. 25, 3389 (1997)), we found that many of the products coded for highly abundant structural RNA species and highly expressed genes. A variety of fragments coding for 16S and 23S rRNA, 50S ribosomal protein and S-layer protein were observed as well as some that shared no homology to other sequences. The inducibility of a representative of each of these products was assessed by performing hybridizations with RNA from untreated or acid-treated cultures. None of the aforementioned products showed acid-inducibility and thus qualified as false-positives. In addition to these products, a 700 bp product, which was not detectable at 0 and 5 minutes, was observed at 15, 30, 45 and 60 minutes after exposure to pH 3.5. Upon sequencing, the translated differential display product shared significant amino acid homology with the gene products of bacterial atpBEF genes. To verify the inducibility of this product, RNA was isolated from acid-treated cultures of L. acidophilus and used as target in an RNA slot blot analysis using the cloned 700 bp fragment as a probe (FIG. 2). The abundance of transcripts increased upon exposure to pH 3.5 and was nearly two-fold greater after 60 min.

Figure 3:
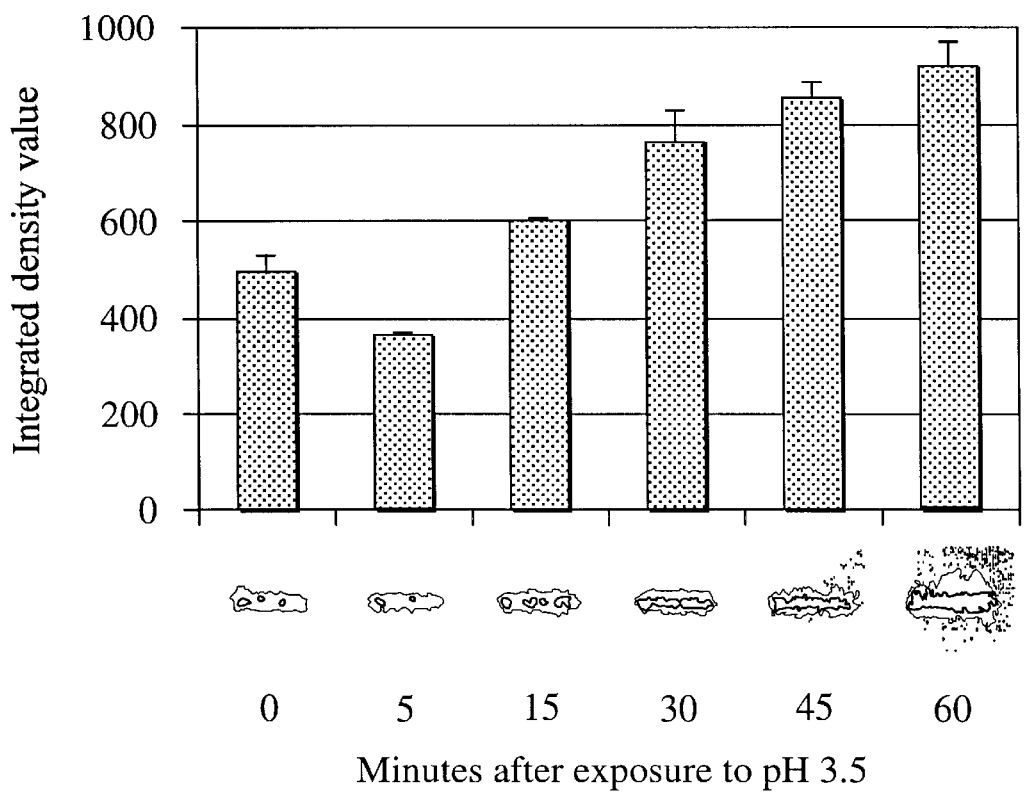
FIG. 3. Slot blot hybridization of RNA from cells incubated at pH 3.5 for various intervals. The slots, each containing 5 μg total RNA, were probed with $^{32}$P-labelled differential display product, comprising atpBEF. The graph represents the results (mean±SEM) of two independent experiments.
Figure 4:
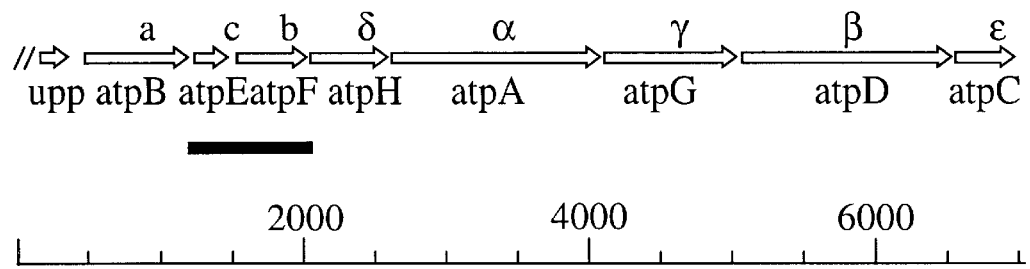
FIG. 4. Specific activity of $H^+$-ATPase (micromoles of inorganic phosphate per minute per milligram of protein) from L. acidophilus at intervals after adjustment of medium pH from 5.6 (time 0) to 3.5.

The hydrolysis of ATP by membrane extracts from L. acidophilus after treatment at pH 3.5 for 0, 15, 30, 45 and 60 minutes was determined (FIG. 4). At pH 5.6 (time 0), the activity of the H$^+$-ATPase was 1.11 μmol P$_i$/min per mg protein. After adjustment of the medium pH to 3.5, the activity of the enzyme quickly increased and was approximately two-fold greater after 30 min. This increase in activity was maintained at 45 and 60 min after exposure to pH 3.5. The timing and level of H$^+$-ATPase activity followed the abundance of atp transcripts observed in RNA blots (FIG. 3), but activities were lower than values reported previously for other organisms (Nannen and Hutkins, supra; Kobayashi et al., supra).

A primer derived from atpF, a portion of which was included in the differential display product, was used in conjunction with a degenerate primer designed from a conserved region of atpD to clone a ca. 4.1 kb internal fragment of the operon. A PCR-based chromosome walking strategy was used to clone the region downstream of atpD to the 3' end of the operon (Ge and Charon, supra). Similar to the problems noted in En. hirae (Shibata et al., *J. Bacteriol.* 174, 6117 (1992)) and *Streptococcus mutans* (Smith et al. *Gene* 183, 87 (1996)), we had difficulty cloning regions upstream of the differential display product, including the putative promoter and the 5' region of atpB. Eventually, single-sided PCR (Shyamala and Ames, supra) on a XbaI-generated genomic plasmid library generated a 2.5 kb product that was an extension of the walking primer. PCR- and restriction enzyme-generated subclones were used to join gaps and resolve ambiguities in the sequence.

The complete nucleotide sequence of the atp operon was determined (data not shown). Eight open reading frames (ORFs) with putative ribosome binding sites (RBSs) and start codons were represented in the sequence of the contiguous clones. The gene order, atpBEFHAGDC, was identical to that observed in other bacteria (Santana et al., supra; Saraste et al. supra; Shibata et al., supra; Walker et al., supra). The start codon of each gene was designated by alignment of atp gene sequences of other bacteria and the position of possible RBSs. TTG start codons appeared to be present for atpA and atpD, while the remaining six genes are proposed to begin with the ATG triplet. The eight gene products of the *L. acidophilus* atp operon were aligned with the ATPase subunits from *E. coli, B. subtilis*, En. hirae and *S. mutans* using the alignment algorithm of Myers et al. (*J. Comput. Biol.* 3, 563 (1996)) with a weight matrix of PAM250 (Table 1). The deduced amino acid sequences of the *L. acidophilus* ATPase subunits showed homology with those of other bacteria. The greatest homology was observed in the α,γ, and β subunits, comprising the cytoplasmic domain ($F_1$) of the ATPase. Less homology was evident for the a, b, and c subunits of the membrane-bound domain. The δ subunit of the $F_1$ domain showed the greatest variability of all the subunits. Of the bacteria included in the comparison, the subunits of the *E. coli* ATPase exhibited the least homology with the corresponding products from *L. acidophilus*. The a, b, and c subunits of the $F_0$ sector from *L. acidophilus* generally appeared most similar to the corresponding protein of B. subtilis, while the α, γ and β subunits of the membrane bound domain shared the greatest homology with *S. mutans* and En. hirae.

TABLE 1

Similarities between the H⁺-ATPase subunits from *L. acidophilus* and other bacteria.

| Gene | Subunit | B. subtilis | E. coli | En. hirae | S. mutans |
|------|---------|-------------|---------|-----------|-----------|
|      |         | % identity (% similarity) | | | |
| atpB | a | 34 (75) | 17 (60) | 36 (74) | 37 (75) |
| atpE | c | 52 (84) | 37 (79) | 43 (64) | 33 (71) |
| atpF | b | 32 (78) | 19 (50) | 37 (79) | 35 (80) |
| atpH | δ | 28 (75) | 25 (74) | 32 (73) | 25 (72) |
| atpA | α | 73 (93) | 51 (86) | 80 (96) | 76 (95) |
| atpG | γ | 33 (75) | 30 (72) | 41 (80) | 35 (78) |
| atpD | β | 61 (88) | 58 (85) | 73 (92) | 71 (90) |
| atpC | ε | 40 (79) | 25 (72) | 42 (70) | 47 (81) |

Sequencing of the 2.5 kb product generated by single sided PCR allowed us to determine the sequence of the 5' region of atpB and upstream nucleotides. Preceding the first gene in the atp operon, atpB, was an ORF with homology to bacterial upp genes, which code for uracil phosphoribosyl-transferases. The upp-atpB intergenic region of *L. acidophilus* was 122 bp long and contained no ORFs. Thus, it appears that the atp operon of *L. acidophilus* does not contain an atpI gene, whose presence in different bacteria is variable (Deckers-Hebestreit and Altendorf, *Annu. Rev. Microbiol.* 50, 791 (1996); Shibata et al. supra; Smith et al. *Gene* 183, 87 (1996)). Interestingly, the initial atpI and atpB genes of the atp operons of *B. subtilis* and *L. acidophilus*, respectively, are each proceeded by the upp gene (Santana et al., *J. Bacteriol.* 176, 6802 (1994)).

Figure 5:
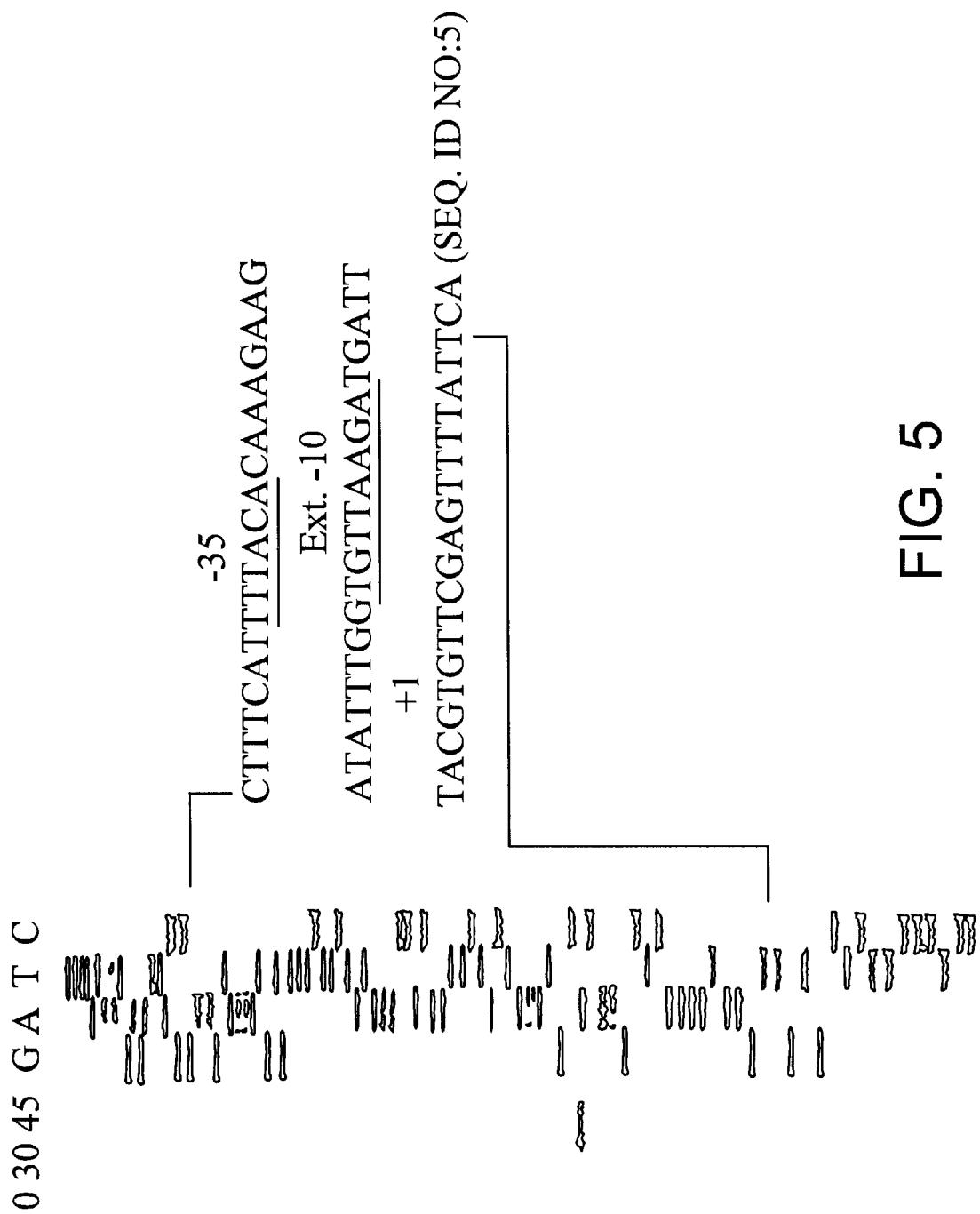
FIG. 5. Part of the nucleotide sequence of the atp operon of L. acidophilus (SEQ ID NO: 5). The transcriptional start site (+1) at position 135 is denoted. Putative −35 and −10 regions are marked with a double underline. Putative ribosome binding sites are underlined with a dashed line. Lower arrows indicate inverted repeats, while the upper arrow shows the region complementary to the primer used for primer extension. The putative nucleotide binding domain of the subunit is indicated by boxing. Amino acids with heavy underlining represent well-conserved residues from which a degenerate PCR primer was based.

Analysis of the nucleotide sequence of the atp operon (SEQ ID NO: 5) revealed several notable features (FIG. 5). An inverted repeat was observed immediately downstream of upp, which may serve as the terminator sequence for this gene. A similar, although stronger, palindromic sequence was observed after atpC. This strong terminator sequence, which is followed by an additional short inverted repeat, shows characteristics of a rho-independent terminator. Other secondary structures were found in the operon, as well. One of these inverted repeats is within the atpE gene, while the other lies immediately downstream of atpE in the 59 bp long atpE-atpF intergenic region. Similar secondary structures, which have been suggested to be involved in the enhanced stability of atpE, have been identified in the atp operons of other bacteria (Das and Ljungdahl, *J. Bacteriol.* 179, 3746 (1997); Santana et al., supra; Walker et al., supra).

Figure 6:
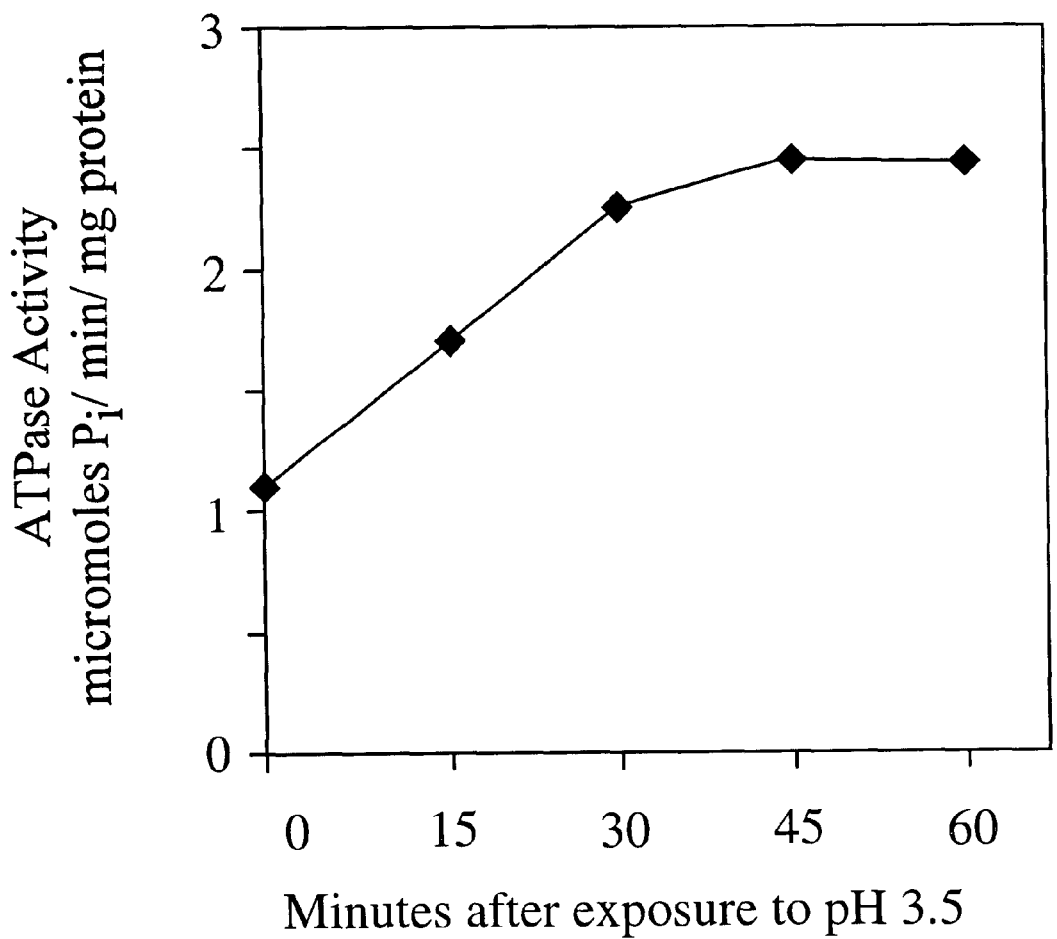
FIG. 6. Primer extension analysis of atp from total RNA isolated at various intervals after exposure to pH 3.5. Lanes containing the products of the primer extension reaction are labeled with the corresponding incubation time. The identified transcriptional start site and upstream sequence are shown.

Primer extension experiments were conducted on RNA extracted from cultures in which the medium pH was shifted from pH 5.6 (time 0) to 3.5 and held for 30 and 45 min (FIG. 6). While the abundance of transcripts appeared to increase in response to pH 3.5, the position of the transcriptional start site (TSS) remained unchanged. These results demonstrated that the TSS of the operon was positioned at a thymine residue, which was 41 nucleotides upstream of the ATG start codon of atpB. At −14 bp from the TSS, a putative extended Pribnow box was identified as having the sequence TGTTAAGAT, which shows 67% identity to the TATAAT −10 consensus sequence of other lactobacilli (Pouwels and Leer, *Antonie van Leeuwenhoek* 64, 85 (1993)) and contains the Gram-positive −16 consensus sequence, TGN (Voskuil et al. *Mol. Microbiol.* 17, 271 (1995)). At −38 bp from the TSS, we observed the sequence TTTACA, which is quite similar to the TTGACA consensus −35 sequence of other Lactobacillus promoters (Pouwels and Leer, supra).

EXAMPLE 2

Ph-Dependent, $P_{311AD}$-Driven Transcription of Cat-86 in *Lactobacillus acidophilus, Lactococcus lactis*, and *L. gasseri*

Figure 7A:
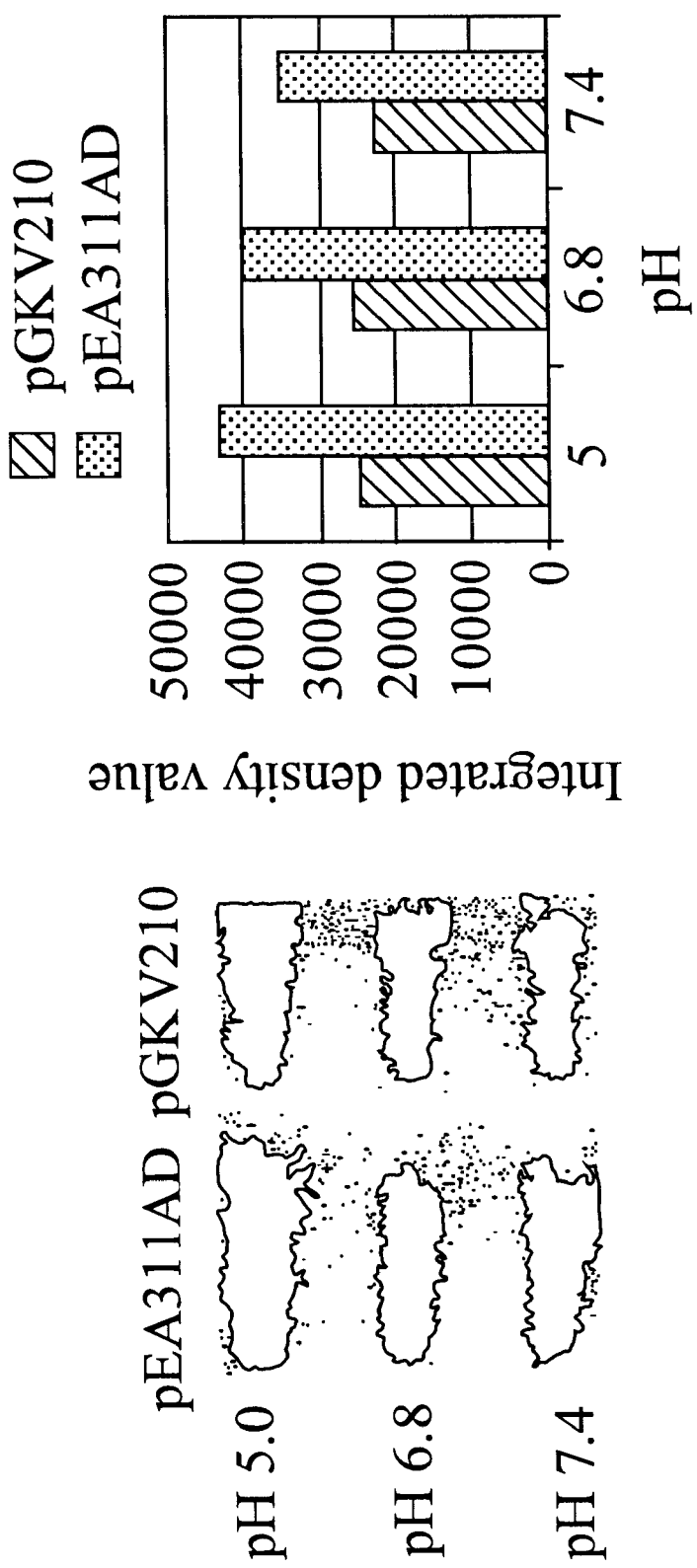
FIG. 7A. pH-dependent, $P_{311AD}$-driven transcription of cat-86 in Lactococcus lactis MG1363 (pH 4.0 HCl and lactic acid-adjusted).
Figure 7B:
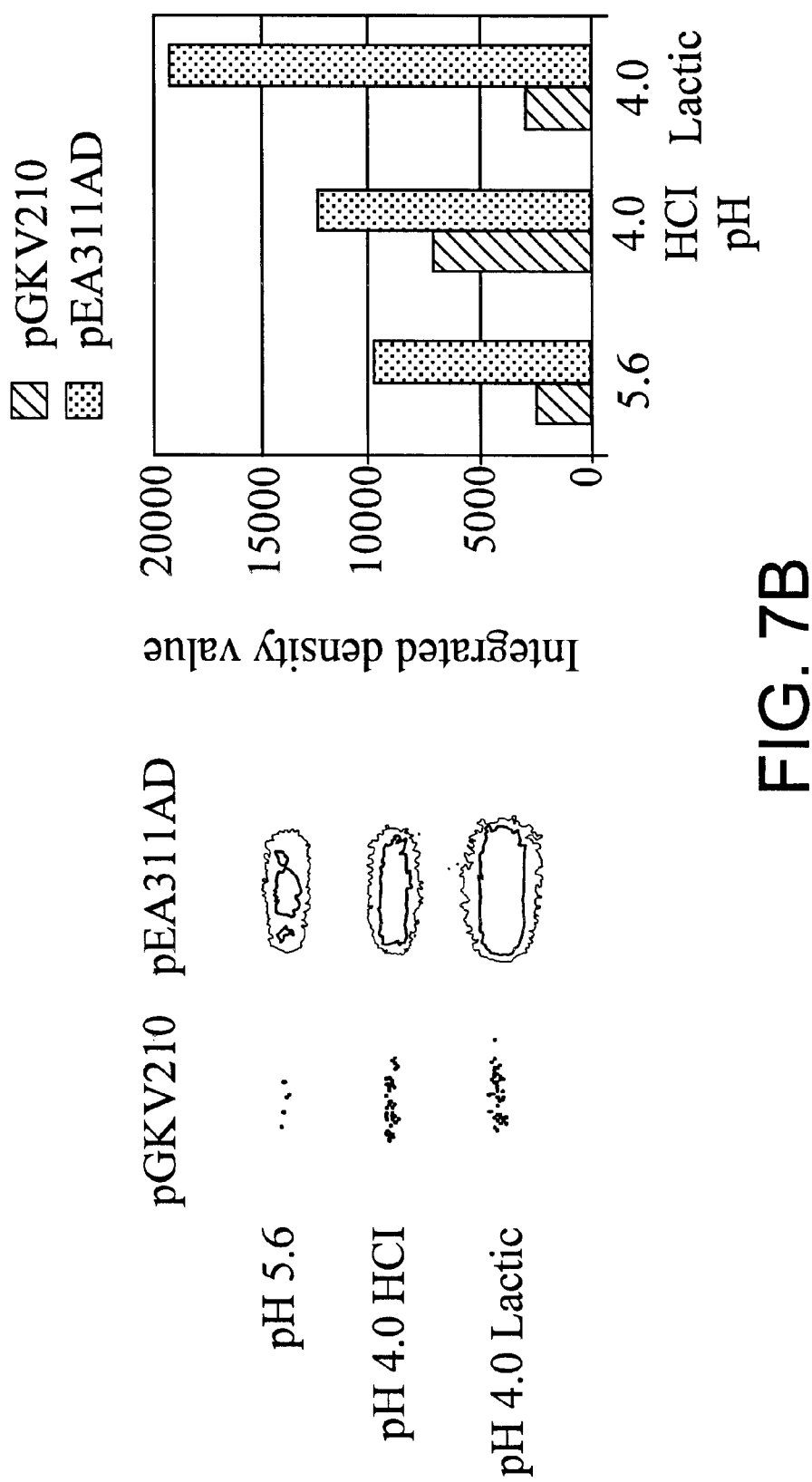
FIG. 7B. pH-dependent, $P_{311AD}$-driven transcription of cat-86 in L. gasseri ATCC 33323 (pH 4.0 HCl and lactic acid-adjusted).

In the present invention, DNA constructs containing the 135 bp $P_{311AD}$ (FIG. 2), situated in front of a heterologous cat-86 gene (chloramphenicol acetyltransferase), were tested for transcriptional activity in the presence of low pH. Promoter-containing constructs were tested for low-pH responsive transcription in Lactococcus (Lc.) lactis MG1363 and in *Lactobacillus gasseri* ATCC 33323. These experiments demonstrated that the transcriptional signals of this promoter were functional and pH-dependent in these backgrounds. In Lc. lactis., medium pH was left unadjusted (pH 7.4) or adjusted to 6.8 or 5.0 with hydrochloric acid, and cat-86 transcripts were measured by hybridization (FIG. 7A). In Lc. lactis, transcripts gradually increased as medium pH decreased and were most abundant at the lowest pH determined, 5.0. In *L. gasseri*, medium pH was adjusted to pH 4.0 with concentrated hydrochloric acid or lactic acid and heterologous cat-86 transcripts were measured by RNA hybridization (FIG. 7B). This experiment demonstrates that the promoter element functions in a low-pH responsive fashion in this host and that induction with lactic acid is considerably greater than that of hydrochloric acid. Southern hybridizations (data not shown) demonstrated the presence of the promoter element in L. acidophilus ATCC 4356 as well as in L. gasseri, L. johnsonii. However, in spite of its functionality in Lc. lactis, the promoter element was not detected by Southern hybridizations in this organism. Together, these experiments demonstrate that $P_{311AD}$ is an acid-responsive promoter that functions in several lactic acid bacteria. Induction of the promoter element can be accomplished with strong or weak (organic) acids.

The foregoing is illustrative of the present invention, and is not to be construed as limiting thereof. The invention is defined by the following claims, with equivalents of the claims to be included therein.

We claim:

1. An isolated polynucleotide encoding an acid inducible promoter selected from the group consisting of:
   (a) DNA having a sequence according to SEQ ID NO: 1 or the complementary strand of SEQ ID NO:1; and
   (b) DNA that hybridizes to DNA of (a) above and under stringent conditions represented by a wash stringency of 50% Formamide with 5×Denhardt's solution, 0.5% SDS and 1×SSPE at 42° C., and encodes an acid-inducible promoter.

2. The isolated polynucleotide of claim 1 having the DNA sequence according to SEQ ID NO: 1.

3. The isolated polynucleotide according to claim 1, wherein said DNA is the *Lactobacillus acidophilus* ATCC 70396 F-type ATPase promoter.

4. A recombinant DNA molecule comprising a promoter operably associated with a DNA of interest, wherein said promoter is an acid inducible promoter selected from the group consisting of:
   (a) DNA having a sequence according to SEQ ID NO:1 or the complementary strand of SEQ ID NO:1; and
   (b) DNA that hybridizes to DNA of (a) above and under stringent conditions represented by a wash stringency of 50% Formamide with 5×Denhardt's solution, 0.5% SDS and 1×SSPE at 42° C., and encodes an acid-inducible promoter.

5. The recombinant DNA molecule according to claim 4, said promoter having the DNA sequence According to SEQ ID NO:1.

6. The recombinant DNA molecule according to claim 4, wherein said DNA of interest encodes a protein or peptide.

7. The recombinant DNA molecule according to claim 4, wherein said DNA of interest encodes an antisense oligonucleotide.

8. The recombinant DNA molecule according to claim 4, wherein said DNA of interest encodes a ribozyme.

9. A vector containing a recombinant DNA molecule according to claim 4.

10. The vector according to claim 9, wherein said vector is a plasmid.

11. A method of transforming a bacterial cell in vitro, comprising:
    providing a vector according to claim 9, and then
    transforming said cell with said vector.

12. A bacterial cell containing a recombinant DNA molecule according to claim 4.

13. The cell according to claim 12, wherein said cell is a lactic acid producing bacteria.

14. The cell according to claim 12, wherein said cell is selected from the group consisting of *Lactobacillus acidophilus, Lactococcus lactis,* and *Lactobacillus gasseri.*

15. The cell according to claim 12, wherein said promoter is operable in said cell.

16. A method of controlling the transcription of a DNA of interest, comprising:
    (a) providing a bacterial cell culture at neutral or basic pH conditions, said culture comprising a cell containing a recombinant DNA molecule, said recombinant DNA molecule comprising a promoter operably associated with a DNA of interest, wherein said promoter is an acid inducible promoter selected from the group consisting of: (I) DNA having a sequence according to SEQ ID NO: 1; and (ii) DNA that hybridizes to DNA of (I) above under stringent conditions represented by a wash stringency of 50% Formamide with 5×Denhardt's solution, 0.5% SDS and 1×SSPE at 42° C. and encodes an acid-inducible promoter; and then
    (b) reducing said pH to acidic conditions so that transcription of said DNA of interest induced by said promoter is increased as compared to the level of transcription of said DNA of interest induced by said promoter when said pH is at neutral or basic conditions.

17. The method according to claim 16, wherein said DNA of interest encodes a protein or peptide.

18. The method according to claim 16, wherein said DNA of interest is transcribed and translated in said bacterial cell.

19. The method according to claim 16, wherein said DNA of interest encodes an antisense oligonucleotide or ribozyme.

20. The method according to claim 16, wherein said cell is a bacterial cell.

21. The method according to claim 16, wherein said step of reducing said pH is carried out by adding an exogenous acid to said bacterial culture.

22. The method according to claim 16, wherein step (b) further comprises reducing said pH is carried out by the fermentative production of an acid by said bacterial culture.

* * * * *

SEQUENCE LISTING

```
<160> NUMBER OF SEQ ID NOS:  5

<210> SEQ ID NO: 1
<211> LENGTH: 135
<212> TYPE: DNA
<213> ORGANISM: Lactobacillus acidophilus

<400> SEQUENCE: 1
cggtactaag taaacacctt ttcacaaaaa atatttactc taatgcgctt tcattttaca      60
caaagaagat atttggtgtt aagatgattt acgtgttcga gttttattca acacgagaag    120
ggaggtcacg aagta                                                     135

<210> SEQ ID NO: 2
<211> LENGTH: 28
<212> TYPE: DNA
<213> ORGANISM: Artificial Sequence
<220> FEATURE:
<223> OTHER INFORMATION: Description of Artificial Sequence:PRIMER

<400> SEQUENCE: 2
tagccgttga accaatgatc ccagtaag                                        28

<210> SEQ ID NO: 3
<211> LENGTH: 28
<212> TYPE: DNA
<213> ORGANISM: Artificial Sequence
<220> FEATURE:
<223> OTHER INFORMATION: Description of Artificial Sequence:PRIMER

<400> SEQUENCE: 3
tagccgttga accaatgatc ccagtaag                                        28

<210> SEQ ID NO: 4
<211> LENGTH: 8
<212> TYPE: PRT
<213> ORGANISM: Artificial Sequence
<220> FEATURE:
<223> OTHER INFORMATION: Description of Artificial Sequence:CONSERVED
      SEQUENCE

<400> SEQUENCE: 4

Ser Ala Val Gly Tyr Gln Pro Thr
  1               5

<210> SEQ ID NO: 5
<211> LENGTH: 63
<212> TYPE: DNA
<213> ORGANISM: Lactobacillus acidophilus

<400> SEQUENCE: 5
ctttcatttt acacaaagaa gatatttggt gttaagatga tttacgtgtt cgagttttat      60
tca                                                                   63
```